United States Patent [19]

Sasaki et al.

[11] Patent Number: 4,975,370

[45] Date of Patent: Dec. 4, 1990

[54] PROCESS FOR PREPARING 14-HYDROXY-6-O-METHYL-ERYTHROMYCIN A

[75] Inventors: Joji Sasaki, Omiya; Kazutoshi Mizoue, Urawa; Takashi Adachi, Kuki; Takatoshi Nagate, Gyoda; Shigeo Morimoto, Saitama; Sadafumi Omura, Ageo, all of Japan

[73] Assignee: Taisho Pharmaceutical Co., Ltd., Japan

[21] Appl. No.: 43,536

[22] Filed: Apr. 28, 1987

[30] Foreign Application Priority Data

May 2, 1986 [JP] Japan .................................. 61-102881

[51] Int. Cl.$^5$ ............................................ C12P 19/62
[52] U.S. Cl. ...................................... 435/76; 435/822; 435/931; 536/7.2
[58] Field of Search .......................... 435/76, 822, 931; 536/7.1, 7.2

[56] References Cited

U.S. PATENT DOCUMENTS

| 4,331,803 | 5/1982 | Watanabe et al. ................... 536/7.2 |
| 4,410,629 | 10/1983 | Terahara et al. ................... 435/135 |
| 4,672,056 | 6/1987 | Fernandes et al. ................... 514/29 |

FOREIGN PATENT DOCUMENTS 58-49396 3/1983 Japan .

*Primary Examiner*—Johnnie R. Brown
*Assistant Examiner*—Elli Peselev
*Attorney, Agent, or Firm*—Lorusso & Loud

[57] ABSTRACT

*Mucor circinelloides* f. *griseo-cyanus* IFO 4563 is cultivated in a medium containing 6-O-methylerythromycin A as a substrate to obtain 14-hydroxy-6-O-methyl-erythromycin A. This compound and its salt have anti-bacterial activity.

4 Claims, 3 Drawing Sheets

PROCESS FOR PREPARING 14-HYDROXY-6-O-METHYL-ERYTHROMYCIN A

BACKGROUND OF THE INVENTION

1. Field of the Invention

The present invention relates to a novel 14-hydroxyerythromycin derivative and a method for preparing the same. More particularly, it relates to 14-hydroxy-6-O-methylerythromycin A, the salts thereof and the method for the production thereof.

2. Description of the Prior Art

An antibiotic 6-O-methylerythromycin A represented by the formula

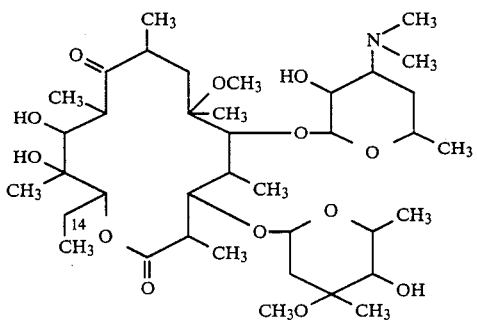

has been invented by a part of the present inventors (U.S. Pat. No. 4,331,803). This compound is an excellent antibiotic, but there is a need for finding out more effective antibiotics.

SUMMARY OF THE INVENTION

As a result of earnest researches to meet the need, the present inventors could prepare a novel compound having a hydroxy group at the 14-position of 6-O-methylerythromycin A by reacting 6-O-methylerythromycin A with a specific microorganism, and thus the present invention has been completed.

Although it is difficult to prepare this compound by chemical means, it can be easily prepared by using the microorganism. Furthermore, this compound has strong in vitro antibacterial activity against Gram-positive bacteria and some Gram-negative bacteria, especially *Neisseria gonorroeae* and *Haemophilus influenzae*, and has stronger in vivo antibacterial activity against some Gram-positive bacteria than 6-O-methylerythromycin A.

An object of the present invention is to provide novel 14-hydroxyerythromycin derivatives having excellent antibacterial activity and a method for easily preparing the same.

DETAILED DESCRIPTION OF THE INVENTION

Figure 1:
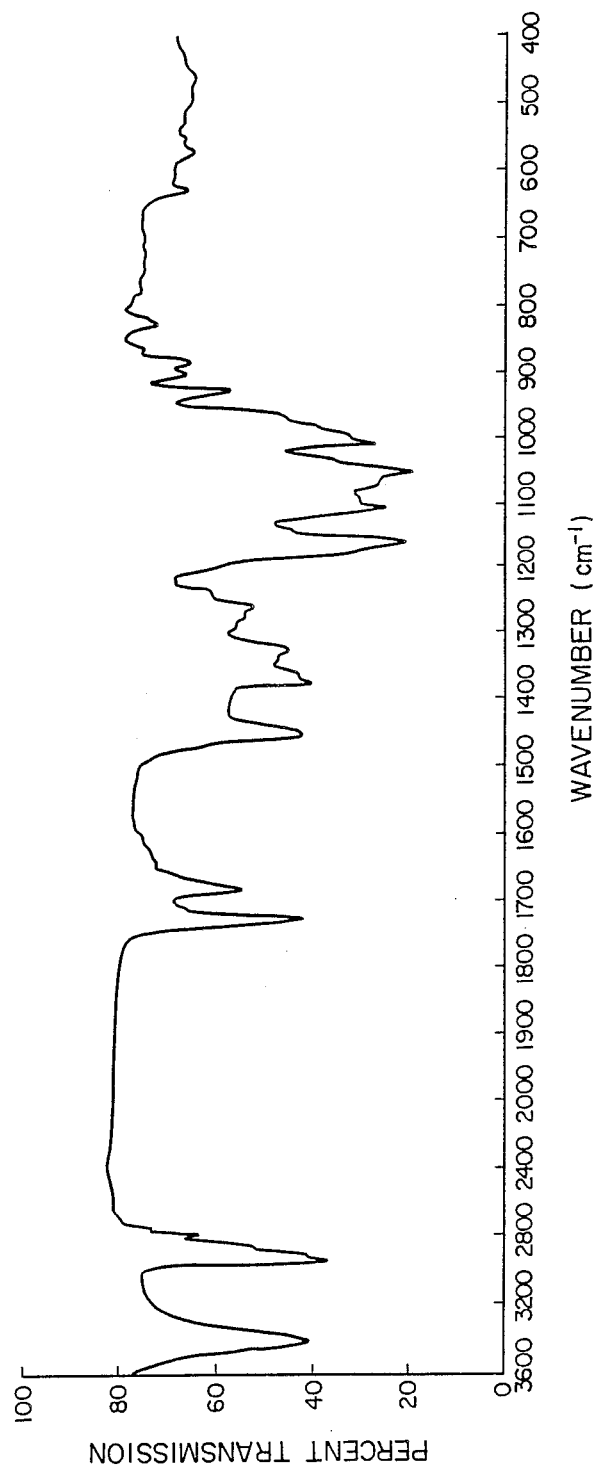
FIG. 1 shows the IR absorption spectrum of 14-hydroxy-6-O-methylerythromycin A measured in KBr tablet.

The compound of the present invention is 14-hydroxy-6-O-methylerythromycin A represented by the formula

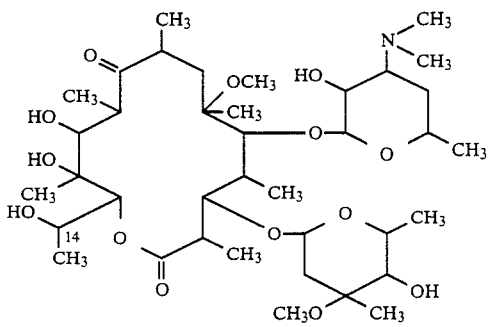

and the salts thereof, and a method for preparing the same which comprises cultivating *Mucor circinelloides* f. griseo-cyanus IFO 4563 in the medium containing 6-O-methylerythromycin A as a substrate.

In the present invention, the term "salt" means pharmaceutically acceptable salts with organic acids such as tartaric acid, citric acid, acetic acid, stearic acid, succinic acid, methanesulfonic acid, aminoethanesulfonic acid and the like; amino acids such as aspartic acid, glutarmic acid and the like.

*Mucor circinelloides* f. griseo-cyanus IFO 4563 is a storage strain at Institute for Fermentation, Osaka and its mycological features are already known. It has been found by the research of the present inventors that this strain has an ability to introduce a hydroxy group to the 14-membered macloride compounds at the 14-position. The method of the present invention can be carried out by cultivating *Mucor circinelloides* f. griseo-cyanus IFO 4563 in the medium containing 6-O-methylerythromycin A under aerobic conditions.

A liquid medium is chiefly used, the carbon sources used are saccharose, glucose and dextrose, and they are used alone or in admixture. Nitrogen sources used are polypeptone, sodium nitrate, yeast extract and the like, and they are used alone or in admixture. In addition, if necessary, organic and inorganic acids can be added in order to aid the growth of the strain and to promote the production of 14-hydroxy-6-O-methylerythromycin A. As defoaming agents can be used Adecanol (produced by Asahi Denka Kogyo Co.), silicon and the like.

Preferred cultivations are aerobic cultivations such as shake cultivation and aerobic stirring cultivation at pH 6 to 7 at a temperature of 28° to 30° C. for 4 to 8 days.

Furthermore, a suitable amount of 6-O-methylerythromycin A is added at the early stage of the cultivation.

Isolation of 14-hydroxy-6-O-methylerythromycin A obtained by the cultivation can be carried out by the common procedures for recovering the fermentation product. Namely, after completion of the cultivation, the culture solution isolated by centrifugation or filtration is adsorbed on a carrier such as DIAION HP 20 (trade name of Mitsubishi Chemical Industrial Co.) and eluted with a lower alcohol, acetone and the like. The eluted fractions containing 14-hydroxy-6-O-methylerythromycin A are concentrated and then crystallized from ethanol to give the crude crystals of 14-hydroxy-6-

O-methylerythromycin A, which are then dissolved in a mixture of chloroform, methanol and aqueous ammonia. The solution is subjected to silica gel column chromatography (e.g., KIESELGEL 60, produced by Merck, West Germany) followed by gel filtration on SEPHADEX LH-20 (trade name of Pharmacia Fine Chemical Co.) with methanol or ethanol as an eluent to isolate 14-hydroxy-6-O-methylerythromycin A.

The physiochemical properties of 14-hydroxy-6-O-methylerythromycin A obtained by the method of the present invention are as follows:

[PHYSIOCHEMICAL PROPERTIES]

(1) Appearance: white needles;
(2) Melting point: 214.5°–216.5° C.;
(3) Elementary analysis:

| Found | Calculated |
|---|---|
| C: 59.27% | C: 59.74% |
| H: 9.12% | H: 9.10% |
| N: 1.95% | N: 1.83% |

(4) Molecular formula: FD and EI mass spectra

FD: $(M+H)^+$ m/z 764

EI: $(M)^+$ m/z 763

Figure 2:
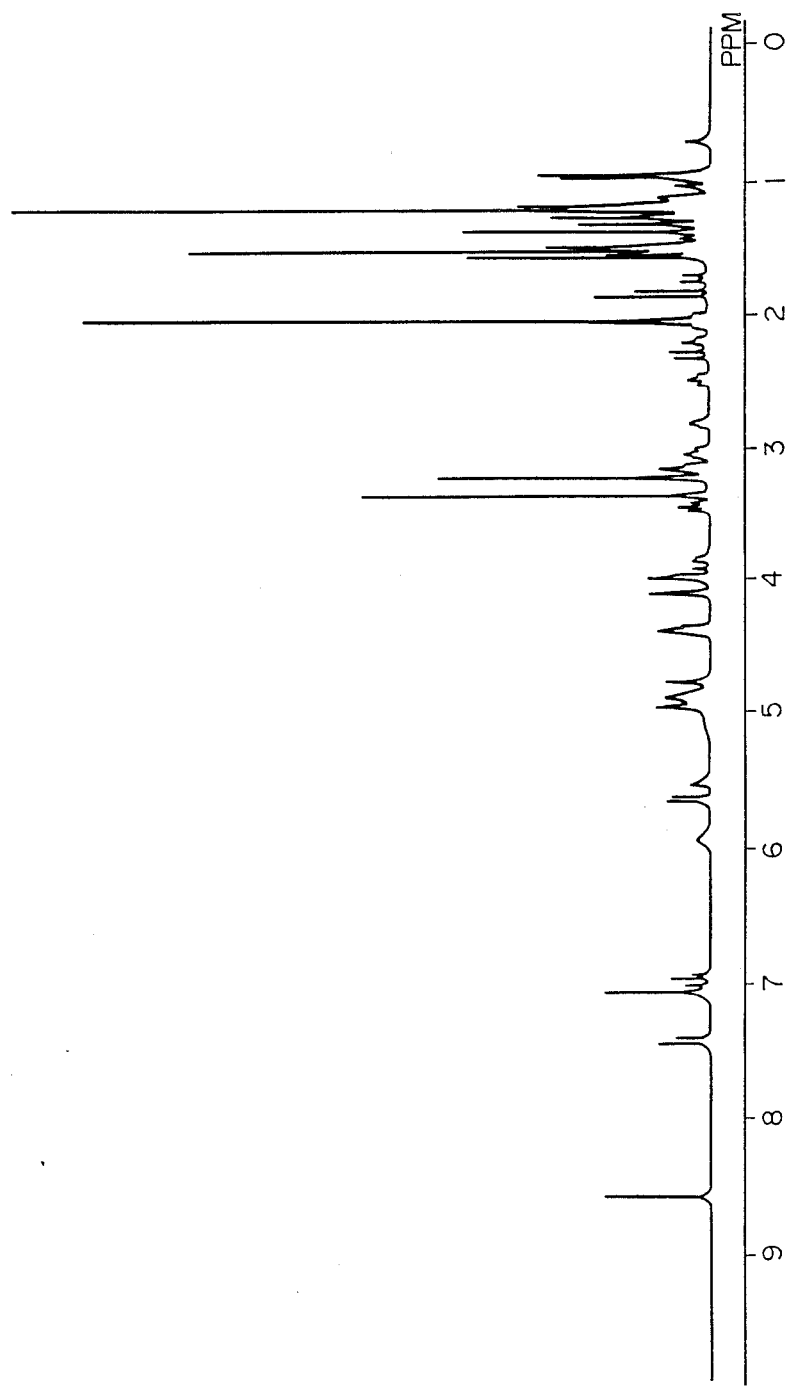
FIG. 2 shows the $^1H$ NMR spectrum of 14-hydroxy-6-O-methylerythromycin A measured in pyridine-d5 at 400 MHz.
Figure 3:
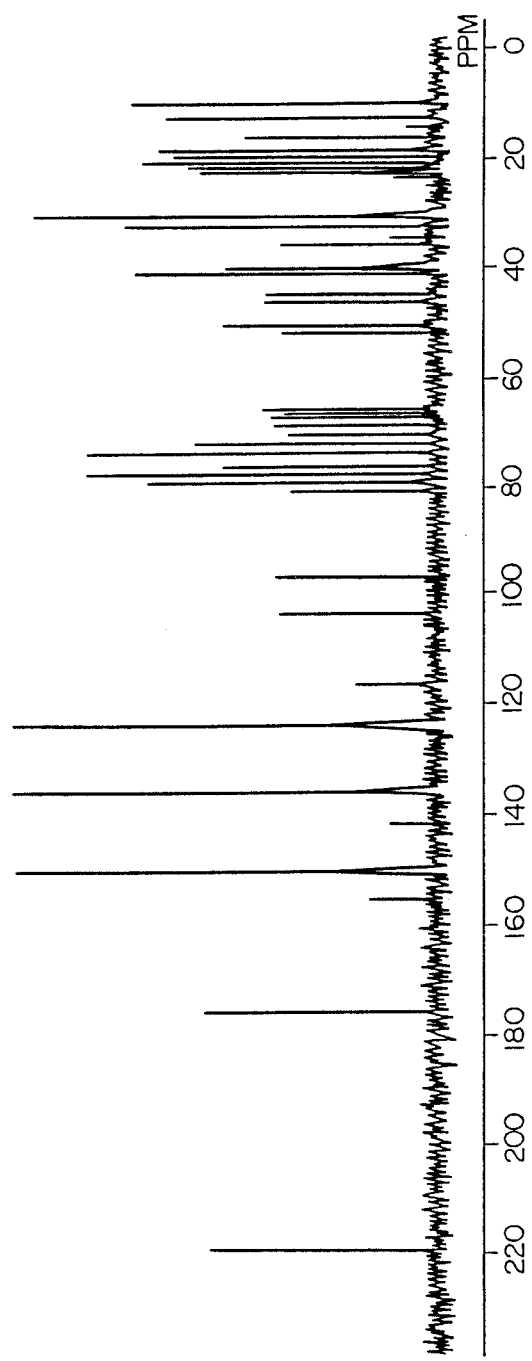
FIG. 3 shows the $^{13}C$-NMR spectrum of 14-hydroxy-6-O-methylerythromycin A measured in pyridine-d5 at 100 MHz.

(5) Molecular formula: $C_{38}H_{69}NO_{14}$
(6) UV absorption: 280 nm ($\epsilon$ 50) in an ethanol solution;
(7) IR absorption spectrum: A spectrum obtained in KBr tablet is shown in FIG. 1.
(8) $^1$H-NMR spectrum: A spectrum obtained in pyridine-d5 at 400 MHz is shown in FIG. 2.
(9) $^{13}$C-NMR spectrum: A spectrum obtained in pyridine-d5 at 100 MHz is shown in FIG. 3.
(10) Solubility:
  Soluble in chloroform, methanol, ethanol, acetone, ethyl acetate and pyridine.
  Poorly soluble in ethyl ether, n-hexane, petroleum ether, benzene and water.
(11) Color reaction:
  positive with sulfuric acid, iodide, anisaldehyde-sulfuric acid and vaniline-sulfuric acid.
  Negative with an aqueous ferric chloride solution and ninhydrin.
(12) Nature: Basic 14-hydroxy-6-O-methylerythromycin A and the salts thereof of the present invention have strong in vitro antibacterial activity against Gram-positive bacteria and some Gram-negative bacteria, especially *Neisseria gonorroeae* and *Haemophilus influenzae*, and have stronger in vivo antibacterial activity against some Gram-positive bacteria than 6-O-methylerythromycin A, and therefore, they can be used as antibiotics. The effective amount ($ED_{50}$) of 14-hydroxy-6-O-methylerythromycin A is from 3 mg/kg to 10 mg/kg of body weight. For the purpose, the compound of the present invention may be administered orally or parenterally in a conventional dosage form such as tablet, capsule, powder, troche, ointment, suspension or solution prepared according to conventional pharmaceutical practices. The $LD_{50}$ value of the compound in ICR mice is 560 mg/kg of body weight by intravanous administration.

As stated above, according to the present invention, it is easy to introduce a hydroxy group to the 14-membered macloride compounds at the 14-position which is hardly prepared by chemical means so that 14-hydroxy-6-O-methylerythromycin A and the salts thereof can be prepared easily and effectively.

The present invention is illustrated in more detail by the following Example and Experiments.

EXAMPLE (1) *Mucor circinelloides* f. griseo-cyanus IFO 4563 was inoculated into a sterile liquid medium (pH 7.0) containing 1% of saccharose, 0.3% of peptone, 0.3% of yeast extract and 50 μg/ml of 6-O-methylerythromycin A, and shake cultivation was carried out at 30° C. for 48 hours to give a seed culture. Then, 30 ml of the seed culture was inoculated into 3 l of a sterile liquid medium (pH 7.0) containing 5% of saccharose, 0.2% of peptone, 0.1% of a yeast extract, 0.1% of dipotassium hydrogen phosphate, 0.05% of potassium chloride, 0.05% of magnesium sulfate and 80 μg/ml of 6-O-methyl-erythromycine A using a 5 l fermentation jar, and fermentation was carried out under the aerobic conditions at 30° C. for 192 hours. Same fermentation was carried out in total 15 ( of the medium using 5 fermentation jars.

(2) After completion of the fermentation, the culture solution was filtered to separate the mycellium and the filtrate. The filtrate thus obtained was adsorbed on 1.5 ( of Diaion HP-20 (trade name, Mitsubishi Chemical Co.) and eluted with 3 ( of ethanol. The eluate was concentrated to give crude crystals of a mixture of 14-hydroxy-6-O-methylerythromycin A and 6-O-methylerythromycin A. The crude crystals were dissolved in a mixture of chloroform, methanol and 25% aqueous ammonia (20:1:0.1 v/v) and adsorbed on a silica gel (Kieselgel 60: trade name of Merck) column packed with the same mixture as that described above. The silica gel column was eluted with 1.2 l of the same mixture as that described above, and the fractions containing 14-hydroxy-6-O-methylerythromycin A were obtained which were confirmed by silica gel thin layer chromatography (Kieselgel 60 F254: trade name of Merck). These fractions were concentrated to dryness to obtain 120 mg of crude 14-hydroxy-6-O-methylerythromycin A as powder.

(3) The crude product obtained in the above item (2) was dissolved in 6 ml of methanol, the solution was subjected to gel filtration on a column of 250 ml of Sephadex LH-20 (trade name of Pharmacia Fine Chemicals) with methanol as an eluent, and the fractions containing 14-hydroxy-6-O-methylerythromycin A were obtained which were confirmed by thin layer chromatography. These fractions were collected and concentrated to dryness and recrystallized from a little amount of ethanol to give about 100 mg of 14-hydroxy-6-O-methyl-erythromycin A as white needles, m.p. 214.5°–216.5° C.

EXPERIMENT 1

(In vitro antibacterial activity)

The antibacterial activity (MIC: minimum inhibitory concentration) of 14-hydroxy-6-O-methylerythromycin A was measured according to the MIC method specified by the Japan Chemotherapeutic Society. The results are shown in Table 1.

TABLE 1

| Test microorganis | MIC (μg/ml) |
|---|---|
| *Staphylococcus aureus* 209P-JC | 0.10 |
| *Staphylococcus aureus* BB | 0.20 |
| *Staphylococcus aureus* Smith 4 | 0.20 |

TABLE 1-continued

| Test microorganis | MIC (μg/ml) |
|---|---|
| *Staphylococcus epidermidis* IID 866 | 0.20 |
| *Staphylococcus pneumoniae* IDD 552 | 0.025 |
| *Staphylococcus pneumoniae* IDD 553 | 0.025 |
| *Staphylococcus pyogenes* IID 689 | 0.025 |
| *Bacillus subtilis* ATCC 6633 | 0.10 |
| *Micrococcus luteus* NIHJ | 0.05 |
| *Micrococcus luteus* ATCC 9341 | 0.025 |
| *Enterococcus faecalis* ATCC 8043 | 0.05 |
| *Escherichia coli* NIHJ JC-2 | 50 |
| *Klebsiella pneumoniae* IFO 3317 | 25 |
| *Salmonella enteritidis* | 25 |
| *Branhamella catarrhalis* | 0.05 |
| *Neisseria gonorrhoeae* TCC-4 | 0.39 |
| *Haemophilus influenzae* J-48 | 3.13 |

EXPERIMENT 2

(In vivo antibacterial test)

The in vivo antibacterial activity of 14-hydroxy-6-O-methylerythromycin A was measured by effect of treatment on experimental infectious diseases in mouse. 6-O-methylerythromycin A and erythromycin A were used as comparative drugs. *Staphylococcus aureus* BB and *Streptococcus pneumoniae* IID 553 were used as experimental infectious diseases of mouse. Ten male ICR mice, weighing 26±1 g, were used for each group to a different concentration of one drug. The bacteria were administered intraperitoneally to each groups of rats for infection. 14-hydroxy-6-O-methylerythromycin A, 6-O-methylerythromycin A and erythromycin A were administered orally to different groups of mice. After observing for 7 days, $ED_{50}$ value was calculated from the number of mice serviving.

The $ED_{50}$ values having 95% confidence limits were estimated by probit analysis. The test results are shown in Table 2.

TABLE 2

| | Bacteria | |
|---|---|---|
| Drug | *Staphylococcus aureus* BB $ED_{50}$ (mg/mouse) | *Streptococcus pneumoniae* IID 553 $ED_{50}$ (mg/mouse) |
| The compound of the present invention | 0.234 | 0.069 |
| 6-O-Methyl-erythromycin A | 0.394 | 0.222 |
| Erythromycin A | 2.20 | 1.43 |

What is claimed is:

1. A process for preparing 14-hydroxy-6-O-methylerthromycin A which comprises cultivating *Mucor circinelloides* f. griseo-cyanus IFO 4563 on a medium containing 6-O-methylerylthromycin A, wherein said cultivating is conducted under aerobic conditions in the presence of a carbon source and a nitrogen source.

2. The process of claim 1 wherein said cultivating is conducted at a pH of 6 to 7 and at a temperature of 28° to 30° C.

3. The process of claim 2 wherein said cultivating is conducted for 4 to 8 days.

4. The process of claim 2 wherein said medium is shaken or stirred during said cultivating.

* * * * *

UNITED STATES PATENT AND TRADEMARK OFFICE
CERTIFICATE OF CORRECTION

PATENT NO. : 4,975,370

DATED : December 4, 1990

INVENTOR(S) : SASAKI et al

It is certified that error appears in the above-identified patent and that said Letters Patent is hereby corrected as shown below:

Col. 4, line 14, "1" should read "$\ell$";

line 19, "1" should read "$\ell$";

line 22, "(" should read "$\ell$";

line 25, "(" should read "$\ell$";

line 27, "(" should read "$\ell$"; and line 36, "1" should read "$\ell$".

Signed and Sealed this

Ninth Day of June, 1992

*Attest:*

DOUGLAS B. COMER

*Attesting Officer*     *Acting Commissioner of Patents and Trademarks*